(12) United States Patent
Palley et al.

(10) Patent No.: US 10,993,660 B2
(45) Date of Patent: May 4, 2021

(54) SYSTEM FOR PHYSIOLOGICAL MONITORING

(71) Applicant: Spire, Inc., San Francisco, CA (US)

(72) Inventors: Jonathan Palley, San Francisco, CA (US); Benjamin Yule, San Francisco, CA (US); Dylan Jackson, San Francisco, CA (US); Zhao Zhao, San Francisco, CA (US); Ross Rudolph, San Francisco, CA (US); Margaret Robb, San Francisco, CA (US); Neema Moraveji, San Francisco, CA (US)

(73) Assignee: SPIRE, INC., San Francisco, CA (US)

( * ) Notice: Subject to any disclaimer, the term of this patent is extended or adjusted under 35 U.S.C. 154(b) by 444 days.

(21) Appl. No.: 15/891,173

(22) Filed: Feb. 7, 2018

(65) Prior Publication Data

US 2018/0220962 A1 Aug. 9, 2018

Related U.S. Application Data

(60) Provisional application No. 62/507,974, filed on May 18, 2017, provisional application No. 62/455,712, filed on Feb. 7, 2017.

(51) Int. Cl.
*A61B 5/08* (2006.01)
*A61B 5/00* (2006.01)
(Continued)

(52) U.S. Cl.
CPC .......... *A61B 5/6804* (2013.01); *A61B 5/0004* (2013.01); *A61B 5/02427* (2013.01);
(Continued)

(58) Field of Classification Search
CPC .... A61B 5/6801; A61B 5/6802; A61B 5/6804
See application file for complete search history.

(56) References Cited

U.S. PATENT DOCUMENTS

| | | | |
|---|---|---|---|
| 4,813,428 | A | 3/1989 | Muraki |
| 5,611,349 | A | 3/1997 | Halleck |

(Continued)

FOREIGN PATENT DOCUMENTS

| | | |
|---|---|---|
| CN | 101917903 | 12/2010 |
| EP | 0699052 | 3/1996 |

OTHER PUBLICATIONS

International Search Report issued in PCT/2018/017275 dated Apr. 23, 2018.

(Continued)

*Primary Examiner* — Puya Agahi
(74) *Attorney, Agent, or Firm* — Knobbe, Martens, Olson & Bear LLP (57) ABSTRACT

A system for monitoring biosignals of a user, including an attachment module configured to secure the system at an inner surface of a garment of the user; a flexible layer coupled to the attachment module, wherein the flexible layer and the attachment module cooperatively define a housing lumen; an electronics subsystem arranged within the housing lumen, the electronics subsystem including a first sensor, wherein the first sensor outputs a first signal; a respiratory sensor, wherein the respiratory sensor outputs a respiration signal, and a processing module that receives the first signal, the respiration signal, and the proximity signal, and generates a processed biometric output based on the first signal and the respiration signals.

18 Claims, 6 Drawing Sheets

(51) Int. Cl.
   *A61B 5/024*    (2006.01)
   *A61B 5/1455*   (2006.01)
   *A61B 5/11*     (2006.01)
   *A61B 5/113*    (2006.01)

(52) U.S. Cl.
   CPC ............ *A61B 5/0816* (2013.01); *A61B 5/113* (2013.01); *A61B 5/1112* (2013.01); *A61B 5/1116* (2013.01); *A61B 5/1118* (2013.01); *A61B 5/14551* (2013.01); *A61B 5/6823* (2013.01); *A61B 5/02438* (2013.01); *A61B 5/6801* (2013.01); *A61B 5/6802* (2013.01); *A61B 5/721* (2013.01); *A61B 2560/0412* (2013.01); *A61B 2562/0219* (2013.01)

(56) References Cited

U.S. PATENT DOCUMENTS

| | | |
|---|---|---|
| 6,480,111 B2 | 11/2002 | Canady |
| 6,936,011 B2 | 8/2005 | Sheldon |
| 8,140,154 B2 | 3/2012 | Donnelly |
| 8,475,371 B2 | 7/2013 | Derchak |
| 8,764,651 B2 | 7/2014 | Tran |
| 9,545,222 B2 | 1/2017 | Derchak |
| 9,699,528 B2 | 7/2017 | Dixit |
| 2006/0122528 A1 | 6/2006 | Gal |
| 2008/0082018 A1 | 4/2008 | Sackner |
| 2008/0108903 A1 | 5/2008 | Ben-Oved |
| 2009/0203972 A1 | 8/2009 | Heneghan |
| 2010/0006106 A1 | 1/2010 | Balakin |
| 2010/0201524 A1 | 8/2010 | Gallagher |
| 2010/0328075 A1 | 12/2010 | Rahamim |
| 2011/0066037 A1 | 3/2011 | Banet |
| 2011/0066038 A1 | 3/2011 | Banet |
| 2011/0130643 A1 | 6/2011 | Derchak |
| 2011/0213271 A1 | 9/2011 | Telfort |
| 2012/0041279 A1 | 2/2012 | Freeman |
| 2012/0220835 A1 | 8/2012 | Chung |
| 2013/0066168 A1 | 3/2013 | Yang |
| 2013/0085538 A1 | 4/2013 | Volpe |
| 2014/0228657 A1* | 8/2014 | Palley ................ A61B 5/14551 600/324 |
| 2014/0358012 A1* | 12/2014 | Richards ............. A61B 5/6802 600/479 |
| 2016/0150982 A1 | 6/2016 | Roy |
| 2016/0192856 A1 | 7/2016 | Lee |
| 2016/0317089 A1 | 11/2016 | Fyfe |
| 2016/0336501 A1 | 11/2016 | Kasichainula |
| 2016/0346584 A1* | 12/2016 | Schneider ............... H01L 27/16 |
| 2017/0325525 A1* | 11/2017 | Hyde ................... A61G 7/1051 |
| 2018/0008195 A1* | 1/2018 | Vaitaitis ............. G08B 21/0453 |
| 2018/0108903 A1 | 4/2018 | Takeda et al. |

OTHER PUBLICATIONS

International Preliminary Report on Patentability issued in PCT/US2018/017275 dated Aug. 13, 2019.

International Preliminary Report on Patentability issued in PCT/US2014/015098 dated Aug. 11, 2015 in 6 pages.

International Search Report issued in PCT/US2014/015098 dated Apr. 16, 2014 in 2 pages.

Extended European Search Report issued in EP 14748473.7 dated Dec. 1, 2016 in 8 pages.

* cited by examiner

SYSTEM FOR PHYSIOLOGICAL MONITORING

CROSS-REFERENCE TO RELATED APPLICATIONS

This application claims the benefit of U.S. Provisional Application No. 62/455,712, filed 7 Feb. 2017, and U.S. Provisional Application No. 62/507,974, filed 18 May 2017, each of which is incorporated herein in its entirety by this reference.

TECHNICAL FIELD

This invention relates generally to the biosignal monitoring device field, and more specifically to a new and useful system and for monitoring biosignals.

BACKGROUND

Respiration parameters can provide profound insight into an individual's wellbeing. Respiration parameters can be indicative of physiological and/or mental states of an individual, as well as prognostic with regard to diagnosis of medical conditions. In examples, respiration parameters and other biometric parameters can provide insight into an individual's stress levels, and can be evidential of more serious pulmonary disorders, such as disorders associated with chronic obstructive pulmonary disease (COPD). Traditionally, however, respiration and other biometric parameter monitoring has occurred in a clinical setting, contributing to the development of respiration monitoring devices that are motion-limiting, lack portability, are not easily integrated into the daily lives of user, and/or are difficult to use. There is thus a need in the biosignal monitoring device field to create a new and useful system for monitoring respiration. This invention provides such a new and useful system and method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System Overview

Figure 1:
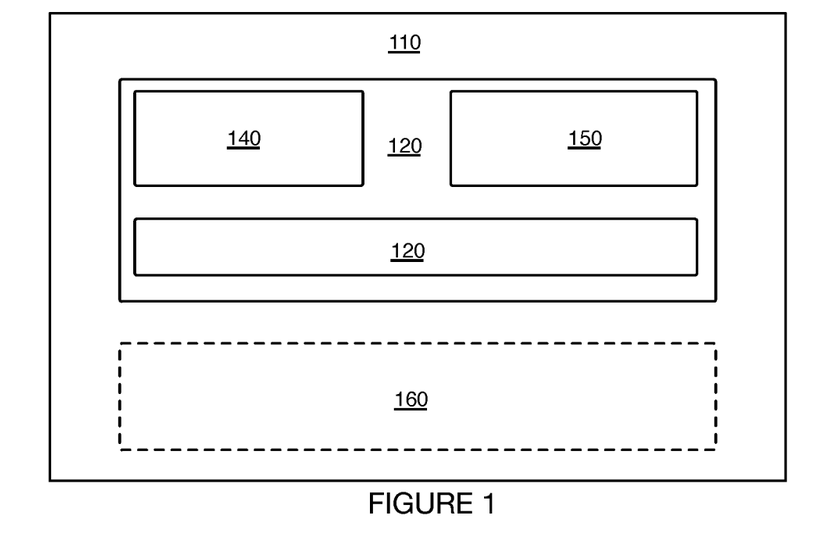
FIG. 1 depicts a schematic of an embodiment of a system for physiological monitoring.

As shown in FIG. 1, an embodiment of a system 100 for monitoring physiological metrics of a user comprises: a housing 110 including an attachment module, and an electronics module 120 including a communication module 130, respiration sensing module 140 and a proximity sensing module 150. The system can, in variations, include a supplementary sensing module 160, as well as any other suitable components. The system can be integrable (e.g., removably couple-able) with garments 900 (e.g., textile-based garments, woven garments, non-woven garments, etc.) such as underwear, brassieres, spandex undergarments, hats, visors, and any other suitable wearable articles. The garments are preferably garments designed to contact the skin of the user (e.g., undergarments), but can additionally or alternatively include outerwear, accessories, and/or any other suitable garments that do or do not directly contact a user's skin.

Figure 5:
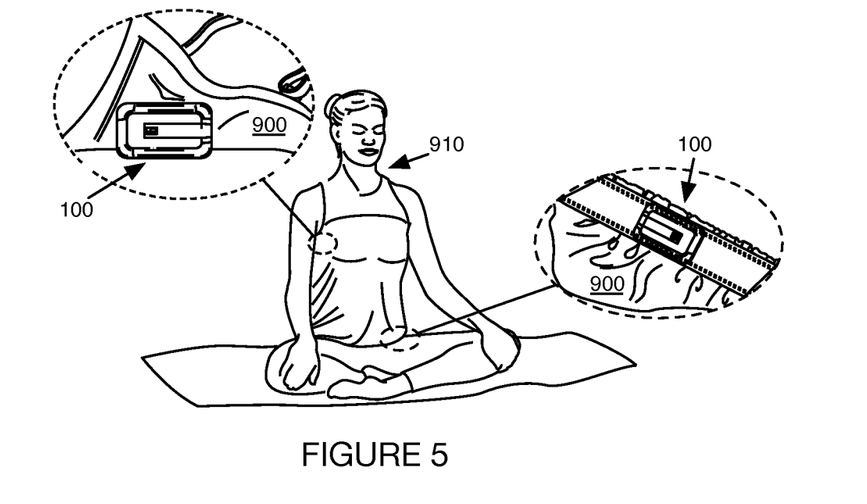
FIG. 5 depicts a plurality of a particular embodiment of the system attached to multiple garments worn by a user during an activity.

In some variations, the system can include multiple instances of the components (e.g., housing, sensing modules, etc.) packaged into discrete system units (e.g., integrated modules). For example, as shown in FIG. 5, the system can include multiple units, each unit coupled to a single garment of a set of garments worn by the user. In another example, the system can include multiple units, each unit coupled to various garments that the user can choose to wear at any given time. However, the system can include one or more units having any suitable correspondence to a set of garments owned and/or worn by the user (e.g., an outfit or outfits).

The system is preferably configured to attach (e.g., by way of the attachment module) to an interior surface of a garment (e.g., waistband, bra, belt, etc.). The powered portions of the system (e.g., the electronics module) are preferably operable between an active mode and a standby mode based on proximity to the user (e.g., based on whether the user is wearing the garment or not). For example, the system can be operable such that motion of the user activates one or more sensor(s) of the system (e.g., a capacitor-based sensor, a piezoelectric transducer for respiratory cadence detection, etc.).

The system is preferably configured such that integration of the system with a garment preserves the physical comfort of the garment and the system does not create discomfort and/or irritation. Thus, the system is preferably manufactured, in whole or in part, out of soft, flexible, and/or resilient materials such as thin films, compressed silicone compounds, woven fabrics, non-woven fabrics, foam substrates, and any other materials suitable for maintaining wearer comfort. Soft-goods manufacturing techniques (e.g., sheet cutting, die cutouts, thermal bonding, sewing, etc.) are preferably used to manufacture components of the system, but additionally or alternatively any suitable manufacturing techniques can be used.

The system 100 functions to provide a garment-integrable system for tracking human physiology metrics. Thus, the system 100 can add physiology-tracking and other sensing capabilities to any suitable garment or wearable article (e.g., a garment that did not previously have such a capability).

The system 100 can additionally or alternatively function to detect signals indicative of a user's respiration characteristics and to provide data relevant to the user's respiration characteristics for further analysis, such that the user's respiration behavior can be monitored. The system 100 can also function to provide information regarding the user's respiration characteristics to the user and/or other entity at a user interface, to monitor and/or indicate physiological and/or mental states of the user based upon the tracked physiological metrics. The system 100 can additionally or alternatively function to facilitate diagnosis of medical conditions with pulmonary indications (e.g., by providing respiratory function data to a physician). The system 100 can additionally or alternatively function to detect signals indicative of any suitable biometric parameters (e.g., photoplethysmography for cardiovascular health monitoring) and provide data relevant to the user's physiological status for further analysis.

2. Benefits

Figure 3A:
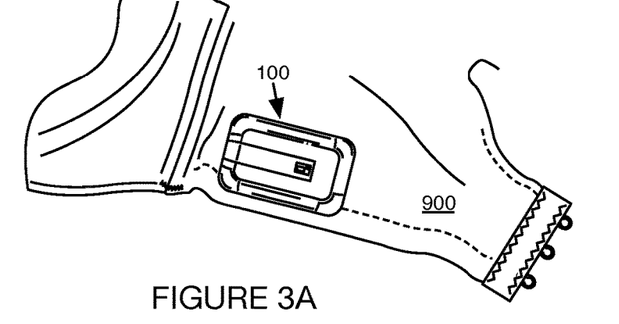
FIGS. 3A-3C depict a variation of an embodiment of the system attached to an internal surface of various garments.
Figure 3B:
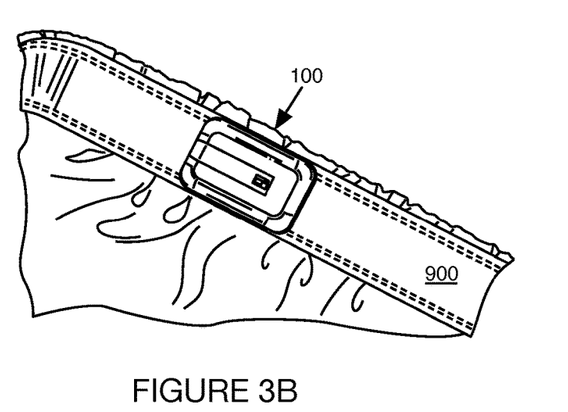
Figure 3C:
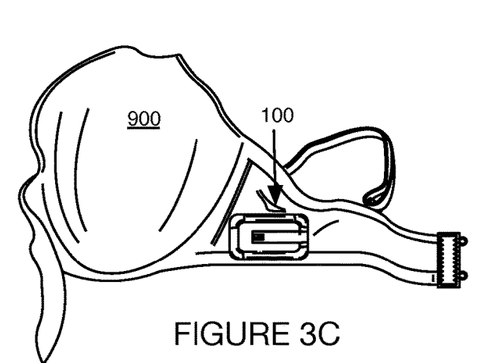
Figure 4A:
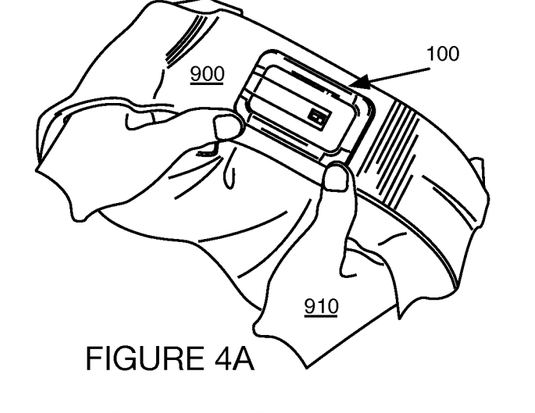
FIGS. 4A-4C depict variations of an embodiment of the system being removed from and/or attached to a garment.
Figure 4B:
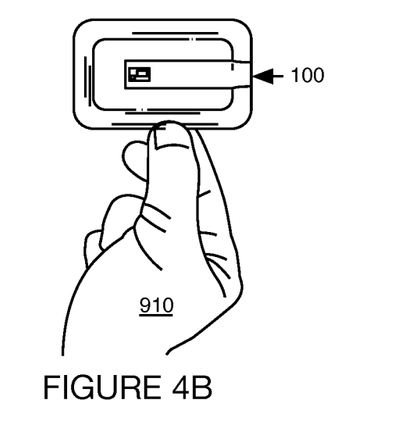
Figure 4C:
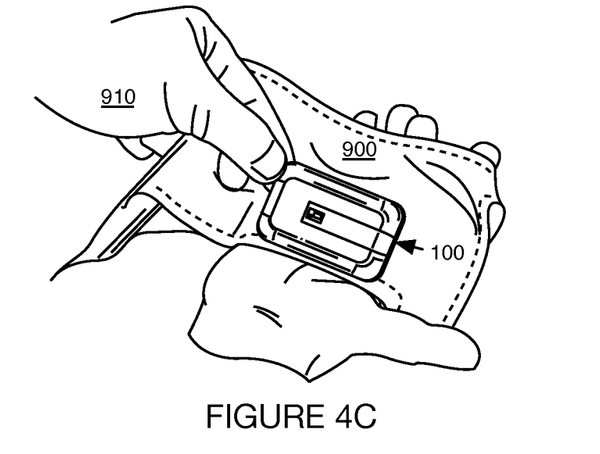

Variations of the system 100 can confer several benefits and/or advantages. First, variants of the system 100 can be temporarily, permanently, or semi-permanently integrated with a user's (e.g., wearer's) existing clothing to facilitate physiological monitoring in a home setting (e.g., in-home monitoring for the elderly) or any other suitable setting. As such, the functionality of the system can be added to any textile, garment, or similar wearable article, independently of the stylistic choices or preferences of the wearer (e.g., because it can be integrated post-purchase into any garment of the user's choice). Examples of garments 900 to which the system can be attached are shown in FIGS. 3A-3C. An example of a user wearing a garment with an attached system as herein described is shown in FIG. 5.

Second, variations of the system 100 can be disposable and reversibly integrated with single-use and/or disposable garments such as hospital gowns, latex gloves, and any other suitable single- or limited-use garments. This can enable physiological monitoring of patients in a hospital setting, scientists in a field setting, or any other suitable entities in any other suitable settings.

Third, variations of the system 100 can be used for local environmental sensing via integration with safety equipment (e.g., carbon monoxide detection for underground miners can be enabled through integration of the system with hardhats worn by the miners).

Fourth, variations of the system 100 can be configured or otherwise assembled to enable features that enhance usability and operation in the context of clothing and wearable articles. For example, variations of the system 100 can be substantially waterproof to enable washing of the system 100 in a washing machine; waterproofing can be achieved in any suitable manner (e.g., via the inclusion of impermeable rubberized encapsulation layers between an inner surface of the housing and the electronics module). Preferably, the system 100 is sufficiently waterproof to withstand at least 60 washing cycles in a washing machine; alternatively, the system 100 can be configured to withstand any suitable number of washing cycles. Variations of the system 100 can additionally be manufactured from materials that do not substantially degrade when heated (e.g., at temperatures commonly reached in a clothes dryer) to allow the system 100 to be attached to clothes that are washed and dried through conventional means.

Fifth, variations of the system 100 can be sufficiently waterproof to enable integration into swimwear and/or wearable articles and/or equipment worn in submerged aqueous environments (e.g., swim caps, goggles, etc.). This can enable monitoring of physiological characteristics and/or parameters of a swimming athlete or individual.

Sixth, variations of the system 100 can provide advantages in the technical field of garment manufacturing, by enabling any manufactured garment to be granted "smart" (e.g., data gathering, physiological monitoring, data transmission, etc.) capabilities by way of the system 100. The garment fabrication manufacturing line need not be retooled to provide these capabilities, because the system 100 can be integrated post-manufacture via the attachment module of the system 100.

Seventh, variations of the system 100 can integrate advantageously with aspects of user behavior and psychology. For example, the user does not need to remember to "put on" the system 100, because it is integrated with garments that the user already wears regularly and/or intends to wear. In some variations of the system 100, the user does not need to remember to actively charge the device, because it harvests energy from the environment (e.g., thermal energy from the user, electrical energy from the user, thermal energy from the washing machine and/or dryer, etc.). Variations of the system 100 can also operate without adhering a sensor to the skin of a user, which can irritate the skin of the user and/or cause excessive discomfort to the user.

Eighth, variations of the system 100 can be configured to have a form-factor suitable for enhancing user comfort and the ability to integrate the system with a garment. For example, the system can be arranged in a layered configuration to provide a compact form-factor that minimizes the occupied volume between an inner surface of the garment and the body of the user, in order to achieve a comfortable fit for the user. The external shape of the system can also be adapted to enhance user comfort; for example, the system can include a bevel about the edge of the system that is smoothly rounded or otherwise shaped to prevent irritation while the garment is worn (e.g., during use cases that cause lateral movement between the user and the system). The materials used to coat the system can be selected in order to enhance user comfort; for example, the system can include an exterior surface layer made of cloth (e.g., natural cloth, synthetic cloth, woven cloth, unwoven cloth, etc.) such that primarily soft materials contact the user when the garment (e.g., to which the system is coupled) is worn.

However, the system 100 can afford any other suitable benefits and/or advantages.

1.1 Housing

Figure 6:
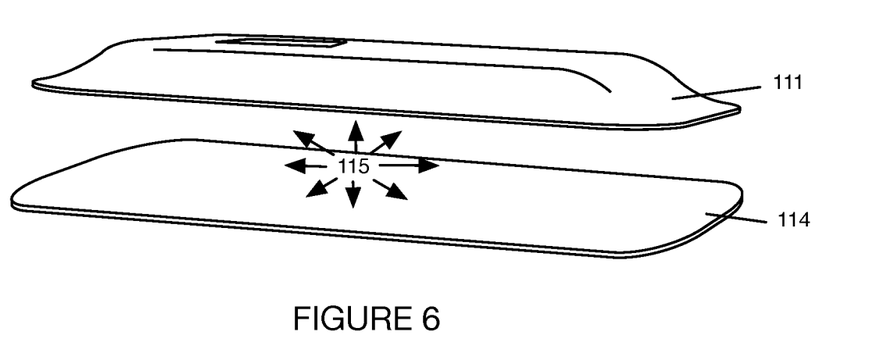
FIG. 6 depicts an exploded view of a portion of a variation of the system.
Figure 11:
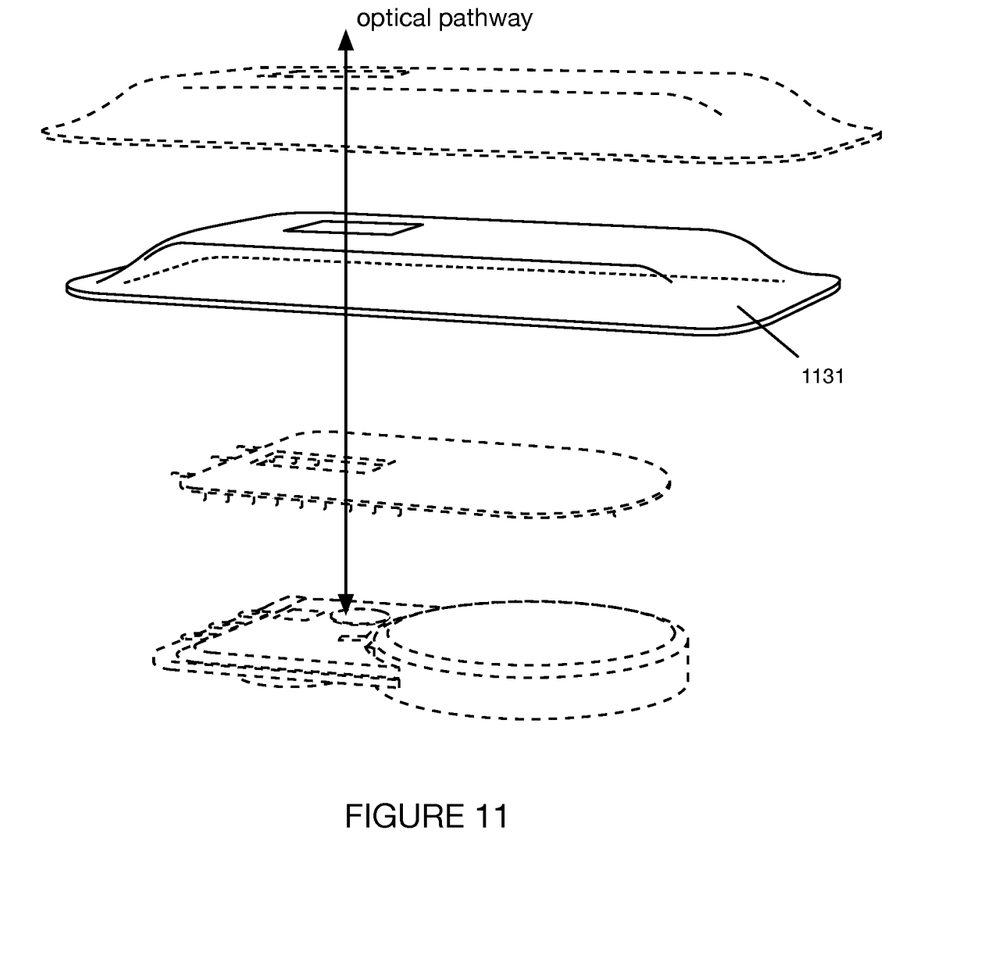
FIG. 11 depicts an exploded perspective view of a portion of an example embodiment of the system, and an example optical pathway therethough.

The housing 110 functions to retain and protect components of the system 100. The housing 110 can provide one or more user-coupling surfaces at which contact sensors of the sensing modules (e.g., respiratory sensing module, proximity sensing module, supplementary sensing module, etc.) can make direct contact with a user (e.g., the skin of a user). The housing 110 can also define one or more openings 112 through which non-contact sensors (e.g., optical sensors) can establish indirect communicative coupling (e.g., an optical pathway as shown in FIG. 11) to the user. The housing 110 preferably includes an outer layer 111, a support structure 113 (e.g., a shell), and an attachment module 114. In variations, the support structure of the housing can be omitted and/or embodied by another portion of the system 100. The housing 110 can optionally include any other suitable components for retaining, supporting, enclosing, or otherwise suitably coupling to components of the system 100 and coupling components of the system to a garment, accessory, and/or a user. The outer layer 111 and attachment module 114 preferably cooperatively enclose the components of the system 100 (e.g., the sensing modules, electronics module, the support structure, etc.) within a housing lumen 115, as shown in FIG. 6, but can additionally or alternatively be otherwise arranged. The support structure of the housing preferably provides structural support to enclosed components of the system 100, such as by ensuring adequate load transfer to force sensors (e.g., touch-sensitive sensors, capacitive touch sensors, etc.) while transmitting loads around components that are not designed to bear substantial load (e.g., printed circuit boards, solder joints, etc.). The support structure can include multiple discrete components; for example, the support structure can include a shell and foam filler material that are discrete components. In another example, the support structure can be made up of a contiguous volumetric body that fills the portions of the housing lumen 115 devoid of other components. However, the support structure can provide structural support in any other suitable manner.

The housing 110 preferably defines a partially deformable lumen and/or volume 115 (e.g., partially defined by a flexible substrate that can be deformed), but can additionally or alternatively define any suitable volume (e.g., a rigid volume). The housing can define a footprint having any suitable shape (e.g., rectangular footprint, polygonal footprint, ellipsoidal footprint, etc.). The housing no can have any suitable geometry, but preferably defines a large aspect ratio (e.g., 2:1) in the projected area, as well as a shallow distance (e.g., between 1 and 10 mm) in the depth direction (e.g., in the direction extending between the user and the interior surface of the garment to which the system 100 is attached). In a specific example, as shown in FIG. 6, the housing defines a housing lumen 115, wherein the housing lumen is cooperatively formed by the attachment module 114 and a flexible outer layer 111 coupled to the attachment module at an edge of the attachment module.

Figure 2:
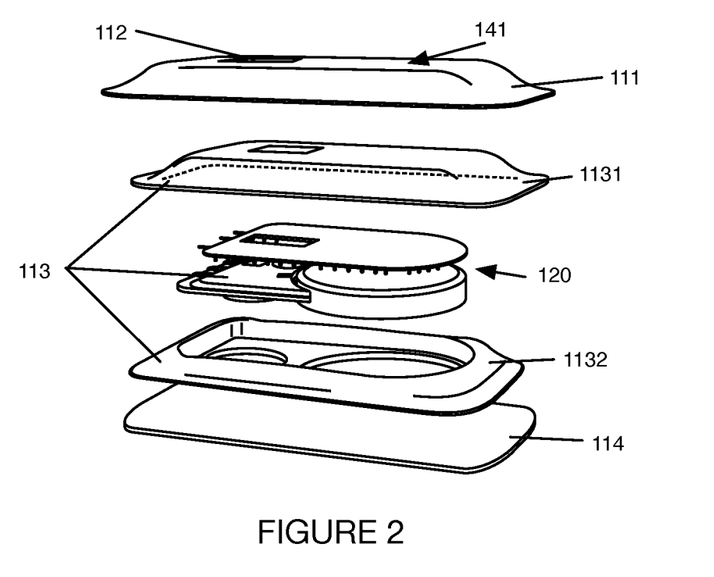
FIG. 2 depicts an exploded view of a specific example of a system for physiological monitoring.

The outer layer 111 of the housing, an example of which is shown in FIG. 2, functions to shield portions of the system 100 from contact with the external environment. At least a portion of the outer layer is preferably manufactured from soft materials (e.g., woven fabrics, non-woven fabrics) to provide a comfortable, non-irritating interface to the user. Accordingly, the outer layer can function to provide a user-coupling interface to the system that is comfortable for the wearer of the garment to which the system is coupled. The outer layer preferably defines at least one opening 112 for a portion of one or more of the respiratory sensing module, proximity sensing module, and the supplementary sensing module to access the external environment; for example, the outer layer can define an opening for a PPG sensor (e.g., as shown in FIG. 11). In some variations, the opening can include a transparent window that physically separates the external environment from a sensor, but permits the passage of electromagnetic radiation (e.g., light) between the interior lumen of the housing and the external environment (e.g., light from an optical pulse oximeter, light gathered by a PPG sensor, etc.). However, the outer layer can be otherwise suitable configured.

The support structure 113 of the housing functions to resiliently retain the components of the system 100 enclosed by the housing to enable operation of the system and prevent breakage. As shown in FIG. 2, the support structure preferably includes a resilient layer 1131 (e.g., a thermally-formed semi-rigid plastic layer) that defines an opening, similar in size, shape, and location to the opening 112 defined in variations of the outer layer. The opening in the support structure can, in a first example, provide a path between the electronics module 120 (e.g., a portion of the electronics module wherein a sensor is located) and the external environment (e.g., by way of a corresponding opening in the outer layer) for one or more sensors (e.g., a PPG sensor).

Figure 9:
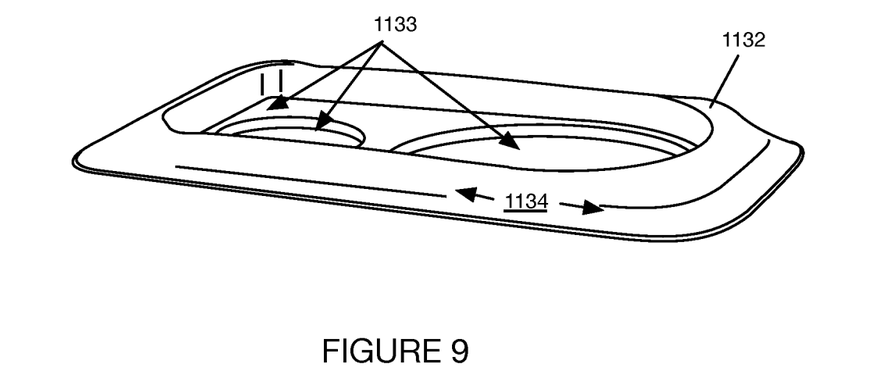
FIG. 9 depicts a perspective view of a portion of a variation of the system.

As shown in FIG. 9, the support structure can include a shell 1132 defining one or more voids 1133, configured to receive and retain the electronics module and sensor modules. The shell is preferably arranged adjacent to the attachment module (e.g., at a surface of the substrate opposing the attachment layer and/or adhesive layer), but can, in variations, be separated from the attachment module by one or more layers and/or other system components. The shell is preferably made up of a resilient material, such as silicone, plastic (e.g., PVC, ABS, HDPE, etc.), high density foam, and the like, but can additionally or alternatively be made up of any suitable material. In a first example, as shown in FIGS. 2 and 9, the shell defines an oblong ellipsoidal depression arranged to receive the electronics module. In another specific example, as shown in FIG. 9, the shell 1132 defines a bevel 1134 about its outer edge that defines the volumetric shape of the system, and is curved such that the external shape minimizes sharp edges or other stark morphological features that could cause user discomfort. The shell can, in variations such as that depicted in FIG. 2, be formed of multiple pieces, wherein a first piece (e.g., piece 1132) defines the one or more voids for receiving components and a second piece defines the external shape and is adapted to couple to the first piece in a stacked configuration (e.g., piece 1131). However, the shell can be otherwise suitably configured.

The support structure 113 can also include foam filler material that occupies portions of the housing lumen defined by the housing that are not otherwise occupied by system components. The foam filler material can, in variations, provide thermal insulation to passively manage heat transfer among components of the system (e.g., including an energy harvesting mechanism that converts thermal energy into electrical energy).

Figure 10A:
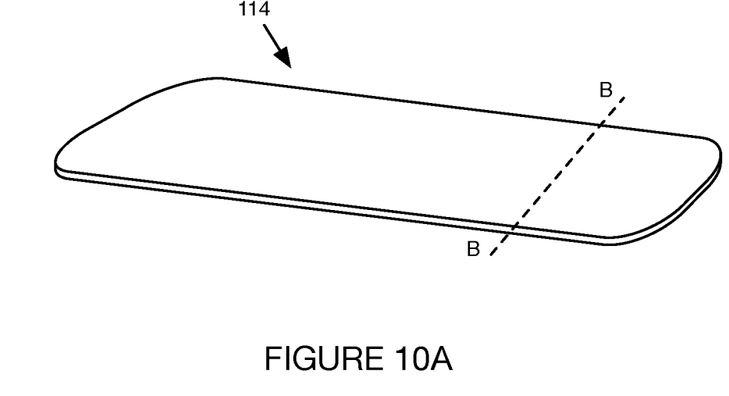
FIGS. 10A-10B depict a perspective view and cutaway view, respectively of a portion of a variation of the system.
Figure 10B:
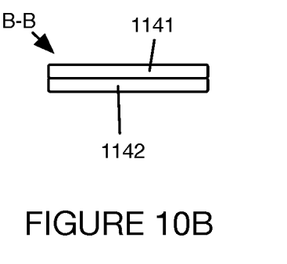

The attachment module 114, an example of which is shown in FIGS. 2 and 10A, functions to couple the system to a wearable article, and to cooperatively enclose components of the system 100 in combination with the outer layer of the housing. The attachment module 114 can include a substrate 1141 and an attachment layer 1142, as shown in FIG. 10B, and any other suitable attachment mechanisms. The substrate is preferably a resilient material (e.g., a polycarbonate substrate), but can additionally or alternatively be any suitable material. The substrate preferably defines a broad surface, at which the attachment layer is arranged. In a first variation the attachment layer 1142 is an adhesive layer, but in alternative variations the attachment layer can include any suitable mechanism for attachment to a wearable article (e.g., one side of a hook-and-loop fastener, one or more buttons, a zipper, etc.).

In a specific example, the adhesive layer includes a two-part silicone elastomer adhesive, wherein the two parts are mechanically mixed upon coupling of the system to a garment. In this example, one of the two parts of the adhesive is preferably encapsulated within the other of the two parts (e.g., within microbeads), but in related examples the two parts can be otherwise oriented in relation to one another prior to mixing (e.g., in separate containers).

The attachment layer preferably covers the entirety of at least one side of the attachment module, but can additionally or alternatively cover any suitable portion of the attachment module and/or other portions of the housing, in whole or in part. In one variation, the system includes an attachment module arranged at opposing sides of the housing, such that the system can be attached to a garment at either of the two opposing sides. In this variation, the attachment module can include one or more openings or otherwise provide for an optical pathway between a sensor of the system (e.g., a PPG sensor) and the skin of the user, in whichever configuration the system is coupled to the user.

1.3 Electronics Module

The electronics module 120 functions to transfer power and control instructions among components of the system 100. The electronics module 120 can additionally or alternatively function to route sensor data between sensors, signal conditioning electronics, control module(s), and communication module(s), as well as to provide a physical substrate for attachment and structural support of electronic components of the system 100. The electronics module can be operable between several modes, including a charging mode. The charging mode can implement a sensor for detecting that the system is in a condition for charging (e.g., via thermal energy harvesting, via inductive charging, via direct electrical connection, etc.). Detecting that the system is in a condition for thermal energy harvesting can include measuring a temperature (e.g., relative to a threshold temperature), measuring a temperature gradient (e.g., relative to a threshold temperature gradient), or determining any other suitable condition in any suitable manner (e.g., according to a laundry schedule, an adaptive schedule that learns the thermal environment of the system as a function of time by iteratively implementing a set of rules, etc.). As such, the system can operate in the charging mode whenever a threshold temperature differential is detected (e.g., after drying of a garment to which the system is coupled, etc.). Detecting that the system is in a condition for inductive charging can include monitoring a voltage and/or current at a node of a signaling circuit, and operating the system in the charging mode in response to the voltage and/or current at the node exceeding a threshold value (e.g., based on a received electromagnetic wave).

The electronics module is preferably arranged within the housing 110 (e.g., supported by a resilient shell 1132 of the support structure of the housing), but can alternatively be otherwise suitably arranged. The electronics module is preferably connected to powered components of the system (e.g., sensor modules, communication module) by way of direct electrical connections (e.g., printed traces and solder joints, flexible jumper wires, etc.), but can be otherwise suitably electrically connected. In variations, the electronics module includes thermally conductive pathways between the external environment of the system and portions of the electronics module (e.g., for thermal energy harvesting at the electronics module). For example, the electronics module can include thermal pathways that direct heat to portions of the electronics module having different thermal properties (e.g., specific heats, thermal conductivities, etc.) that cause a voltage to be generated in the presence of a temperature gradient, and further include electrical circuitry to harvest (e.g., store) energy from the generated voltage. The electronics module 120 can include one or more sensors 121, a substrate 122, a battery 123, charging circuitry 124, and a signal processing module 125. The electronics module 120 can also include a communication module 130, a respiration sensing module 140, and a proximity sensing module 150. The electronics module preferably includes a printed circuit board to which each of the components of the electronics module is electrically and/or mechanically coupled. However, the electronics module 120 can additionally or alternatively include any suitable electronic components.

The substrate 122 of the electronics module functions to provide a physical attachment location, structure support, and integrated electronic connectivity to system components. In a specific example, the substrate 122 includes a printed circuit board (PCB). However, the substrate can additionally or alternatively include any suitable electronic component attachment and/or support mechanism.

The battery 123 of the electronics module functions to store and provide electrical power to components of the system. In a specific example, the battery is a non-chargeable 2032 coin cell lithium battery. In another specific example, the battery is a rechargeable cell (e.g., lithium polymer battery pack). However, the battery can additionally or alternatively include any suitable power storage and delivery device (e.g., a capacitor) and/or any other suitable chargeable and/or non-chargeable device.

The charging circuitry 124 of the electronics module functions to convert energy from various forms into a form usable by the system (e.g., to electrical energy). Forms of energy convertible by the charging circuitry include thermal energy, electromagnetic (e.g., inductively-coupled, capacitively-coupled, propagating) energy, mechanical energy (e.g., generated by movement of the wearer and captured using an eccentric rotary pendulum), and any other suitable form of energy. The charging circuitry can include a battery capacity monitor. In a specific example, the battery capacity monitor includes a known resistance load, and is operable between a monitoring mode and a non-monitoring mode. The monitoring mode includes switching the battery terminals across the load of known resistance, measuring the voltage drop across the load, and computing the state of the battery based on the measured voltage (e.g., the state of the battery as represented by a point on a current-voltage characteristic curve).

In a first variation, the charging circuitry can function to harvest thermal energy. In this variation, the charging circuitry includes one or more heat flux channels (e.g., thermally conductive pathways surrounded by thermally insulating material) and a thermal energy converter. The heat flux channels preferably define thermally conductive paths extending away from an external surface of the system and toward the charging circuitry, and are in direct thermal contact with portions of the charging circuitry (e.g., the thermal energy converter). The external surface can be user-coupling (e.g., to extract thermal energy from a user's body heat), in contact with the ambient environment (e.g., to extract thermal energy from ambient heat), or any other suitable external surface. In a specific example, the charging circuitry includes a housing segment, a heat collector, thermally conductive filler material, and a heat flux channel arranged in series between the external surface and the charging circuitry.

In a second variation, the charging circuitry can function to harvest ambient radiofrequency (RF) energy. In this variation, the charging circuitry includes one or more conductive loops arranged within the housing; in examples, the conductive loops can be arranged to maximize the circumscribed area of each loop (e.g., around the perimeter of the internal lumen of the housing) at multiple azimuthal angles about an axis of the system. The charging circuitry in this variation can also include RF power conversion circuitry coupled to the conductive loops and configured to transform voltage generated by background RF (and/or other electromagnetic radiation) waves passing through the conductive loops into stored electrical energy. Background RF can be incidentally generated, and thus include wireless router signals (e.g., generated as part of an in-home wireless internet network), cellular radio signals, or any other suitable background RF signals. RF radiation can additionally or alternatively be generated for the purpose of powering the system (e.g., the system can be placed in a drawer with RF-reflective walls, wherein RF radiation is injected into the drawer which acts as a lossy cavity from which the charging circuitry can harvest energy) or for any other suitable purpose.

In a third variation, the charging circuitry functions to inductively charge the system. In this variation, the charging circuitry includes a secondary coil coupled to the battery. The secondary coil is inductively coupled to the primary coil of a charging station (e.g., a charging element of a base station), which generates alternating-current waveforms through the primary coil that induce alternating-current waveforms in the secondary coil. Energy can then be harvested by the charging circuitry from the induced alternating-current waveforms.

The signal processing module of the electronics module functions to process signals generated by sensing modules and/or other components of the system. The signal processing module can include a processor. The signal processing module can be operated between several modes, including a sampling mode. The sampling mode can include cascade sampling of multiple sensor modules, in which samples are collected from the multiple sensor modules sequentially. The sampling mode can additionally or alternatively include sampling from each sensor module in a synchronized manner (e.g., collecting samples from each sensor module substantially simultaneously). However, the signal processing module can be otherwise operated in any suitable mode to perform any suitable signal processing function. Furthermore, signal processing associated with the system 100 can additionally or alternatively be implemented in the cloud (i.e., using remote processing systems, such as Amazon Web Services cloud computing services, using other cloud computing platforms, etc.) in relation to one or more of data transmission, data processing, data storage, data retrieval, and/or any other suitable processing relation functions.

1.2.A Communications Module

The communication module 130 functions to enable pairing of the system 100 with a database. The communication module 130 can also function to transmit gathered data for reception by a computing system. The communication module can be operable between several modes, including a pairing mode, a broadcasting mode, and an encoding mode. The pairing mode can include communicating with a hub (e.g., a base station) in order to identify the instance of the system 100 being worn by the user (e.g., in cases in which the user wears various garments, each of which is integrated with an instance of the system) and establish a data link between the system and a network connected to the base station (e.g., the internet). The broadcasting mode can include transmitting data (e.g., over a Bluetooth link) for collection (e.g., by a base station, by a mobile device, etc.). The encoding mode can include storing data at a storage module of the system for later retrieval. In a first variation, the encoding mode includes reconfiguring an internal circuit (e.g., an FPGA) of the communication module to modulate a signal according to a pattern that encodes a recorded data set, such that the data set can be communicated as a modulated signal (e.g., a modulated radio signal, a modulated inductive charging signal, etc.). In a specific example implementation of the encoding mode, heart rate data is encoded and stored in onboard memory as a state of a modulator of the communication module, and during inductive charging of the system the current transmission between the system and the inductive charger is modulated according to the modulator state and the modulated current is read at the inductive charger (e.g., the base station) and decoded as heart rate data.

The communication module preferably includes at least one radio (e.g., Bluetooth, Bluetooth low energy, Bluetooth smart, cellular, or any other suitable radio). In variations, the communication module includes multiple radios corresponding to different frequency bands and/or communication protocols, for use in different circumstances (e.g., a cellular radio that turns on when the system is fully charged for high bandwidth transmission, and a BLE/BTsmart radio that wakes periodically for low power burst transmissions at lower bandwidth). However, the communication module can include any suitable number of any suitable communication mechanisms. The communication module is preferably arranged within the housing (e.g., supported by the silicone shell of the support structure of the housing), and is preferably coupled to (e.g., powered by) the electronics module, but can be otherwise suitable arranged and otherwise Suitably Connected.

1.2.B Respiration Sensing Module

The respiration sensing module 140 functions to measure the respiratory function of a user of the system. Measuring the respiratory function can include detecting a set of signals indicative of a set of respiratory characteristics of the user. The respiration sensing module 140 can include a sensor 121 configured to detect a set of signals indicative of a set of respiration characteristics (e.g., respiration signals) of the user, and functions to sense movement of a portion of the user's body, wherein the movement results from the user's respiration. At least a portion of the respiration sensing module 140 is preferably in direct force-contact with the user (e.g., with the user's clothing, with the user's skin) in a manner that provides robust force transmission between the user and the respiration sensing module at a sensor-user interface 141. The sensor-user interface can be at the external surface of the system 100, in variations wherein the respiration sensor is contained within the housing lumen, and include solid system components (e.g., portions of the support structure) that transmit force to the force sensor of the respiration sensing module. However, in additional or alternative variations, portions of the respiration sensing module 140 are disposed at the exterior surface of the system 100 and are in direct adjacent contact with the user. After coupling, the sensor-user interface is preferably substantially fixed, such that motion detection associated with breathing can be easily distinguished from any other motion (e.g., gross motions of the user). The sensor-user interface is preferably located proximal to the user's torso (e.g., abdomen region, hip region, chest region); however, the sensor-user interface can be located at any suitable location relative to the user. Alternatively, the sensor-user interface can be non-fixed, and the system 100 can be configured to distinguish motion of the user's body associated with breathing from other detected motions (e.g., motion of the sensor relative to the user's body, gross motions of the user).

Preferably, the sensor of the respiration sensing module 140 functions to detect motions of the user's chest and/or abdominal wall produced during the user's breathing. Additionally, the respiration sensing module 140 is preferably non-invasive in detecting signals indicative of the user's respiration behavior; however, the respiration sensing module 140 can comprise invasive or minimally invasive elements. Alternatively, the respiration sensing module 140 can function based upon any other suitable plethysmography-based sensing method, any other suitable mechanical sensing method (e.g., acoustic sensing), and/or any suitable sensing method (e.g., ultrasound respiration sensing). Additionally, the respiration sensing module 140 preferably detects signals indicative of the user's respiration characteristics substantially continuously and in real time; however, the respiration sensing module 140 can alternatively or additionally detect signals intermittently and/or not in real time.

In a first variation, the respiration sensing module 140 preferably comprises a sensor including at least one element configured to deflect (e.g., in compression) in response to movements of the user's body produced by the user's breathing. The element of the sensor is preferably configured to provide a robust connection with the user, such that deflections associated with the user's breathing are detected with minimal interference due to other motions of the user and/or sensor. In the first variation, the respiration sensing module can thus be positioned between the user's clothing and the user's skin, coupled robustly to an article of the user's clothing, and/or coupled to the user using any one or more of an adhesive (e.g., permanent adhesive, non-permanent adhesive), strap, clip, or other suitable coupling element.

Figure 7A:
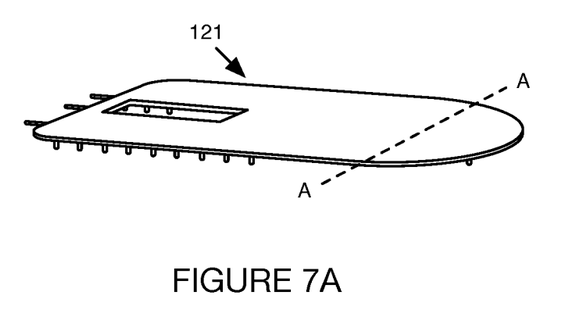
FIGS. 7A-7B depict a perspective view and cutaway view, respectively of a portion of a variation of the system.
Figure 7B:
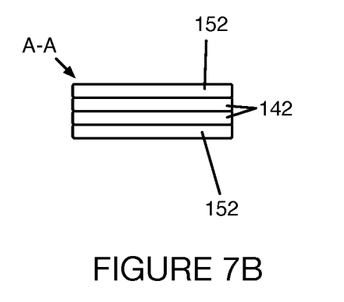
Figure 8:
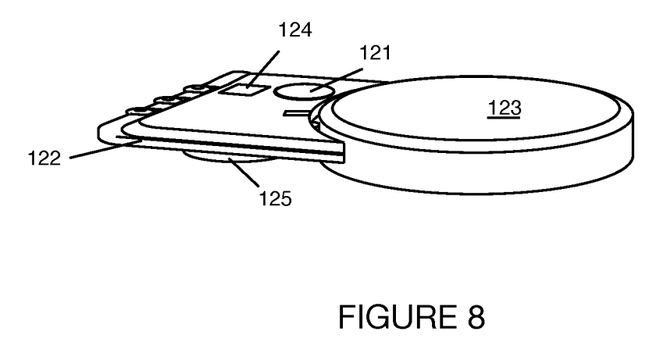
FIG. 8 depicts a perspective view of a portion of a variation of the system.

In a first example of the first variation, as shown in FIG. 7, the respiration sensor 142 comprises two layers of a capacitive sensor 121 having four layers. The two layers from which the respiration sensor signal is generated are, in this example, the innermost two layers. However, in related examples, the layers from which the respiration sensor signal can be the outermost two layers, or any other suitable combination of two layers of a capacitive sensor having any suitable number of layers.

Variations of the respiration sensor can, however, include any suitable embodiment, variation, or example of the respiration sensors and methods of use thereof described in U.S. application Ser. No. 14/174,466, titled "System and Method for Monitoring Respiration", and filed on 6 Feb. 2014, which is herein incorporated in its entirety by this reference.

The set of respiration characteristics preferably comprises any one or more of: respiration rate (e.g., breaths per second), depth of breath, shallowness of breath, thoracic variations, tidal volume (or an estimation thereof), inspiratory flow (e.g., peak value, mean value), expiratory flow (e.g., peak value, mean value), fractional inspiratory time, work of breathing, phase angle, any other suitable respiration characteristic, and any other suitable derivative of a respiration characteristic. Additionally, the set of respiration characteristics detected by the respiration sensing module 140 can indicate respiration events associated with laughter, sighing, wheezing, coughing, apnea, and/or any other suitable event associated with the user's respiration.

1.2.C Proximity Sensing Module

The proximity sensing module 150 functions to detect when the garment with which the system 100 is integrated is being worn by the user (e.g., in order to operate the system in a low-power-mode to preserve battery power when not in use). The proximity sensing module 150 preferably includes at least one proximity sensor 151 that generates a signal indicative of the proximity of the user to the system 100. In a specific example, as shown in FIG. 7, the proximity sensor 151 comprises two layers 152 of a capacitive sensor 121 having four layers. The two layers from which the proximity sensor signal is generated are, in this example, the outermost two layers. However, in related examples, the layers from which the respiration sensor signal is generated can be the innermost two layers, or any other suitable combination of two layers of a capacitive sensor having any suitable number of layers. As such, a dual-region or multi-region capacitive sensor having multiple layers can provide regions associated with respiration sensing, and regions associated with capacitive sensing.

The proximity sensing module can optionally include an accelerometer, a temperature sensor, and/or any other suitable sensor that can collect data indicative that the garment to which the system is attached is being worn by a user. For example, accelerometer data can be analyzed to determine that the system is proximal an individual that is walking or running, and the system (e.g., the signal processing module of the system) can determine that the garment with which the system is integrated is being worn. In another example, the temperature sensor of the proximity sensing module can detect a temperature within a range of normal body temperatures (e.g., 98 degrees Fahrenheit) of a human, and the system can thus determine that the sensor is proximal a wearer of the garment. However, the proximity sensing module 150 can otherwise suitably determine the proximity of the system to a user and/or whether the garment attached to the system is presently being worn.

The supplementary sensing module 160 functions to detect a supplemental set of signals from the user. The supplementary sensing module 160 can additionally function to provide additional data that facilitates processing of the set of signals indicative of the set of respiration characteristics. The supplementary sensing module 160 can include one or more: accelerometers, gyroscopes, digital compasses, analog compasses, pressure sensors (e.g., barometric pressure sensors), temperature sensors (e.g., thermocouples, thermistors), optical sensors (e.g., optical heart rate sensors), digital bio-impedance sensors, microphones (e.g., MEMS based microphone for acoustic sensing), PPG sensors, and any other suitable sensors. Outputs of the sensor(s) of the supplementary sensing module 160 can form the basis for any suitable actions of the previously described operating modes, as well as any other suitable operating modes (e.g., the system can be operated in a charging mode based on a measurement of a temperature sensor of the supplementary sensing module).

1.5 Specific Examples

In a first specific example, as shown in FIG. 1i, the system includes a photoplethysmographic (PPG) sensor that detects a pulse oximeter signal at the skin of the user, and combines the pulse oximeter signal with a signal from an accelerometer to mitigate artifacts produced in the pulse oximeter signal due to bulk movement of the user. In a related specific example, the system includes a force sensor that generates a touch force signal proportional to movement of the user's skin proximal a contact point of a PPG sensor of the system, and combines the touch force signal with the signal from the PPG sensor to mitigate artifacts in the signal resulting from skin movement of the user. In this example, the respiration sensor and proximity sensor are integrated into a single capacitive sensor comprising four layers, wherein the innermost layers generate the proximity sensing signal and the outermost layers generate the respiration sensor signal. The capacitive sensor, in this example, also defines an opening through which the PPG sensor extends from the electronics module to an external surface of the system (e.g., as shown in FIG. 11). Accordingly, in this example, the capacitive sensor is arranged in a stacked configuration between the electronics module and the shell of the housing.

In a second specific example, data from the accelerometer can be used to distinguish motion of the user not associated with the user's respiration characteristics from motion of the user associated with the user's respiration characteristics. For example, motion of the user associated with walking or exercising may produce signal detection at the respiration sensing module, and the accelerometer can be used to separate interfering data resulting from walking or exercising from data directly associated with the user's respiration characteristics. As such, the accelerometer data can be used to filter out interfering data in order to extract data relevant to the user's respiration characteristics. The accelerometer can be a single axis accelerometer, but can also be a dual- or triple-axis accelerometer. Furthermore, data from the accelerometer can function to provide enriching data associated with, for example, the user's posture (e.g., upright, laying down, slouching, sitting, etc.) and/or the user's activity (e.g., exercise, resting, sleeping, etc.).

In a third specific example, data from the gyroscope can be used to distinguish motion of the user not associated with the user's respiration characteristics from motion of the user associated with the user's respiration characteristics. The gyroscope thus functions to detect orientation of the system 100, which can be used to facilitate data processing and/or can be used to enrich data for further analyses. For example, motion of the user associated with laying down or sitting upright may produce signal detection at the respiration sensing module, and the gyroscope can be used to separate interfering data resulting from laying down or sitting upright from data directly associated with the user's respiration characteristics. As such, the gyroscope data can be used to filter out interfering data in order to extract data relevant to the user's respiration characteristics. The gyroscope can be a single axis accelerometer, but can also be a dual- or triple-axis gyroscope. Furthermore, data from the gyroscope can function to provide enriching data associated with, for example, the user's posture (e.g., upright, laying down, slouching, sitting, etc.) and/or the user's activity (e.g., exercise, resting, sleeping, etc.).

In a fourth specific example, data from the GPS can indicate that the user is at a gym, and can be used to provide a label or tag for respiration signals collected while the user is at the gym. In another example, data from the GPS can indicate that the user is in a stressful environment (e.g., examination room, hospital, etc.) and can be used to provide a label or tag for respiration signals collected while the user is in the stressful environment. In yet another example, data from the GPS can indicate that the user is in a non-stressful environment (e.g., restaurant, home) and can be used to provide a label or tag for respiration signals collected while the user is in the non-stressful environment. Data from the GPS and/or other sensors of the supplementary sensing module 120 can additionally or alternatively be used to guide the user in monitoring his/her respiration behavior once the system 100 detects that the user is in any suitable environment. For example, data from the GPS can be used to guide the user's breathing behavior once the GPS and/or accelerometer has indicated that the user is exercising.

In a fifth specific example embodiment, the system includes an attachment module defining a first surface and a second surface opposing the first surface, wherein the first surface includes an adhesive layer that secures the system at an inner surface of a skin-contacting garment wearable by the user. The example embodiment also includes a shell arranged at the second surface of the attachment module, wherein the shell defines a recessed region, and wherein the shell defines a bevel about an outer edge of the shell. The example embodiment also includes a flexible layer attached to the second surface of the attachment module and enclosing the shell, wherein the flexible layer defines a first opening. The example embodiment also includes an electronics subsystem arranged within the recessed region between the shell and the flexible layer. The electronics subsystem of the example embodiment includes a first sensor, wherein the first sensor is an optical sensor that outputs a first signal, wherein the first signal can be associated with one or more cardiovascular parameters including one or more of: heart rate, heart rate variability, blood pressure, blood pressure variability, measures of blood vessel stiffness, measures indicative of atherosclerosis, and/or other relevant cardiovascular health parameters.

The electronics subsystem of the example embodiment also includes a set of capacitive layers arranged between the first sensor and the flexible layer, a first pair of the set of capacitive layers acting as a respiratory sensor and second pair of the set of capacitive layers acting as a proximity sensor, wherein the set of capacitive layers defines a second opening aligned with the first opening and the optical sensor of the first sensor. The respiratory sensor outputs a respiration signal, and the proximity sensor outputs a proximity signal. The electronics subsystem of the example embodiment includes a processing module that receives the first signal, the respiration signal, and the proximity signal, outputs a processed biometric output based on the first signal and respiration signal, and controls the electronics subsystem based on the proximity signal.

The first sensor of the fifth example embodiment can be a photoplethysmographic (PPG) sensor that defines an optical pathway that extends through the first and second openings, away from the attachment module. The electronics subsystem of the fifth example embodiment can include an energy harvesting mechanism. In particular, the energy harvesting mechanism can be operable between a harvesting mode and a standby mode, by the processing module, based on the proximity signal. The harvesting mode can include converting thermal energy into electric energy and powering the electronics subsystem using the electric energy, and the standby mode can include passively storing the electric energy.

A sixth specific example embodiment includes an attachment module configured to secure the system at an inner surface of a garment of the user. The sixth example embodiment also includes a flexible layer coupled to the attachment module, wherein the flexible layer and the attachment module cooperatively define a housing lumen. The sixth example embodiment also includes an electronics subsystem arranged within the housing lumen. The electronics subsystem of the sixth example embodiment includes a first sensor that outputs a first signal, a respiratory sensor that outputs a respiration signal, and a processing module. The processing module receives the first signal, the respiration signal, and the proximity signal, and generates a processed biometric output based on the first signal and respiration signal.

The attachment module of the sixth example embodiment can include an adhesive layer that semi-permanently bonds the attachment module to the garment of the user.

The first sensor of the sixth example embodiment can be an optical sensor (e.g., a PPG sensor) and the respiratory sensor can be a force sensor (e.g., a capacitive touch sensor). In such cases, the processing module can modify the first signal based on the respiration signal in generating the processed biometric output. In particular, the processing module can determine a set of signal artifacts based on the respiration signal and remove the set of signal artifacts from the first signal in generating the processed biometric output. However, the processing module can otherwise suitably process the respiration signals.

The sixth example embodiment can include a shell arranged within the housing lumen, wherein the shell defines a recessed region and a bevel about an outer edge of the shell. In such cases, the electronics subsystem can be arranged within the recessed region of the shell.

The electronics subsystem of the sixth example embodiment can include a proximity sensor, and can be operable between an active mode and a standby mode based on a proximity signal output by the proximity sensor. The active mode can include powering the first sensor and respiratory sensor and processing the first signal and respiration signal at the processing module. The standby mode can include passively maintaining the first sensor and respiratory sensor in an off state. In some examples, the proximity sensor can be made up of a first pair of capacitive layers, and the respiratory sensor can be made up of a second pair of capacitive layers. The first and second pairs of capacitive layers can be contiguous, and can be arranged between the first sensor and the flexible layer of the sixth example embodiment. In a related example, the second pair of capacitive layers is arranged between the first pair of capacitive layers, and wherein the first and second pairs of capacitive layers define an opening through which the first sensor is exposed (e.g., optically exposed).

The electronics subsystem of the sixth example embodiment can include an energy harvesting mechanism, and the processing module can be configured to control the energy harvesting module between a harvesting mode and a standby mode. as described above in relation to the fifth example embodiment. The processing module can additionally or alternatively be configured to control the energy harvesting module between the harvesting mode and the standby mode based on a temperature signal output by a temperature sensor of the electronics subsystem, wherein the harvesting mode includes converting thermal energy into electric energy and powering the electronics subsystem using the electric energy, and wherein the standby mode includes passively storing the electric energy. The processing module can also be configured to control the energy harvesting module between the harvesting mode and the standby mode based on the proximity signal, or based on any other suitable signal. In a related example, the harvesting mode can include converting mechanical energy into electric energy and powering the electronics subsystem using the electric energy.

The electronics subsystem of the sixth example embodiment can include a data storage module (e.g., portion of the communication module) operable between a plurality of modes including an encoding mode. The data storage module can include an internal circuit (e.g., a field programmable gate array). The encoding mode can include reconfiguring the internal circuit such that the internal circuit modulates an input signal to produce an output signal, wherein the output signal encodes the processed biometric output.

Variations of the system 100 can include any combination or permutation of the described components, processes, and/or operating modes. Furthermore, various processes of the preferred method and/or operation modes or techniques of the system can be embodied and/or implemented at least in part as a machine configured to receive a computer-readable medium storing computer-readable instructions. The instructions are preferably executed by computer-executable components preferably integrated with a system and one or more portions of the control module 155 and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for monitoring physiological data of a user, comprising:
   an attachment layer comprising a first surface and a second surface opposing the first surface, wherein the first surface comprises an adhesive configured to secure the system at an inner surface of a garment wearable by the user to position the system between the garment and a body of the user;
   a flexible layer attached to the second surface of the attachment layer to form an interior volume, wherein the flexible layer comprises a first opening; and
   electronics positioned in the interior volume, the electronics comprising:
   an optical sensor configured to output a first signal;
   a set of stacked capacitive layers, a first pair of the set of stacked capacitive layers forming a respiratory sensor and second pair of the set of stacked capacitive layers forming a proximity sensor, the first pair of capacitive layers of the respiratory sensor being arranged between the second pair of capacitive layers of the proximity sensor, wherein the set of stacked capacitive layers includes a second opening aligned with the first opening and the optical sensor, wherein the respiratory sensor is configured to output a respiration signal, and wherein the proximity sensor is configured to output a proximity signal, and a processor configured to receive the first signal, the respiration signal, and the proximity signal, determine physiological data based on the first signal and the respiration signal, and control the electronics based on the proximity signal.

2. The system of claim 1, wherein the optical sensor comprises a photoplethysmographic (PPG) sensor configured to monitor a physiological property of the user through an optical pathway that extends through the first and second openings.

3. The system of claim 1, wherein the electronics further comprises an energy harvester.

4. The system of claim 3, wherein the processor is configured to switch the energy harvester between an energy harvesting mode and a standby mode responsive to the proximity signal.

5. The system of claim 3, wherein the processor is configured to switch the energy harvester between an energy harvesting mode and a standby mode, and wherein, in the energy harvesting mode, the energy harvester converts thermal energy into electric energy during at least one of washing or drying of the garment, and powers the electronics with the electric energy, and wherein the standby mode comprises passively storing the electric energy.

6. The system of claim 1, wherein the adhesive is configured to semi-permanently bond the attachment layer to the garment of the user.

7. The system of claim 1, wherein the processor is configured to modify the first signal based on the respiration signal in determining the physiological data.

8. The system of claim 7, wherein the processor is configured to determine a set of signal artifacts based on the respiration signal and remove the set of signal artifacts from the first signal in determining the physiological data.

9. The system of claim 1, wherein the electronics is configured to switch between an active mode and a standby mode responsive to the proximity signal output by the proximity sensor, wherein the active mode comprises powering the optical sensor and the respiratory sensor and processing the first signal and the respiration signal with the processor, and wherein the standby mode comprises maintaining the optical sensor and the respiratory sensor in an off state.

10. The system of claim 5, wherein electronics further comprises a temperature sensor configured to measure temperature, and wherein the processor is configured to switch the energy harvester responsive to the measured temperature.

11. The system of claim 1, wherein the electronics further comprises electronic circuitry configured to encode the physiological data using a modulation scheme.

12. The system of claim 11, wherein the electronic circuitry comprises a field programmable gate array.

13. The system of claim 1, wherein the flexible layer is configured to transmit a force resulting from movement of the body of the user caused by respiration of the user to the set of stacked capacitive layers, and wherein a capacitive layer of the first pair of the set of stacked capacitive layers is configured to deflect in response to the transmitted force.

14. The system of claim 1, wherein the first opening comprises a transparent window.

15. The system of claim 8, wherein the set of signal artifacts are indicative of force resulting from movement of the body of the user caused by respiration of the user, and wherein the respiratory sensor is configured to detect the force.

16. The system of claim 1, further comprising a recess in the interior volume, wherein the electronics is at least partially positioned in the recess.

17. The system of claim 16, wherein the electronics comprises a power source positioned in the recess.

18. The system of claim 1, further comprising an accelerometer configured to detect motion of the user, wherein the electronics is further configured to, responsive to a detection of the motion by the accelerometer, activate the respiratory sensor.

* * * * *

UNITED STATES PATENT AND TRADEMARK OFFICE
CERTIFICATE OF CORRECTION

PATENT NO. : 10,993,660 B2
APPLICATION NO. : 15/891173
DATED : May 4, 2021
INVENTOR(S) : Jonathan Paul K. Palley Page 1 of 1

It is certified that error appears in the above-identified patent and that said Letters Patent is hereby corrected as shown below:

In the Specification

In Column 5, Line 28, delete "no" and insert --110--.

In Column 10, Lines 26-27, delete "Suitably Connected." and insert --suitably connected.--.

In Column 12, Line 55, delete "1i," and insert --11,--.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*